Feb. 16, 1965 J. R. MITTLEIDER Plant Pat. 2,475
DIANTHUS PLANT
Filed Sept. 23, 1963
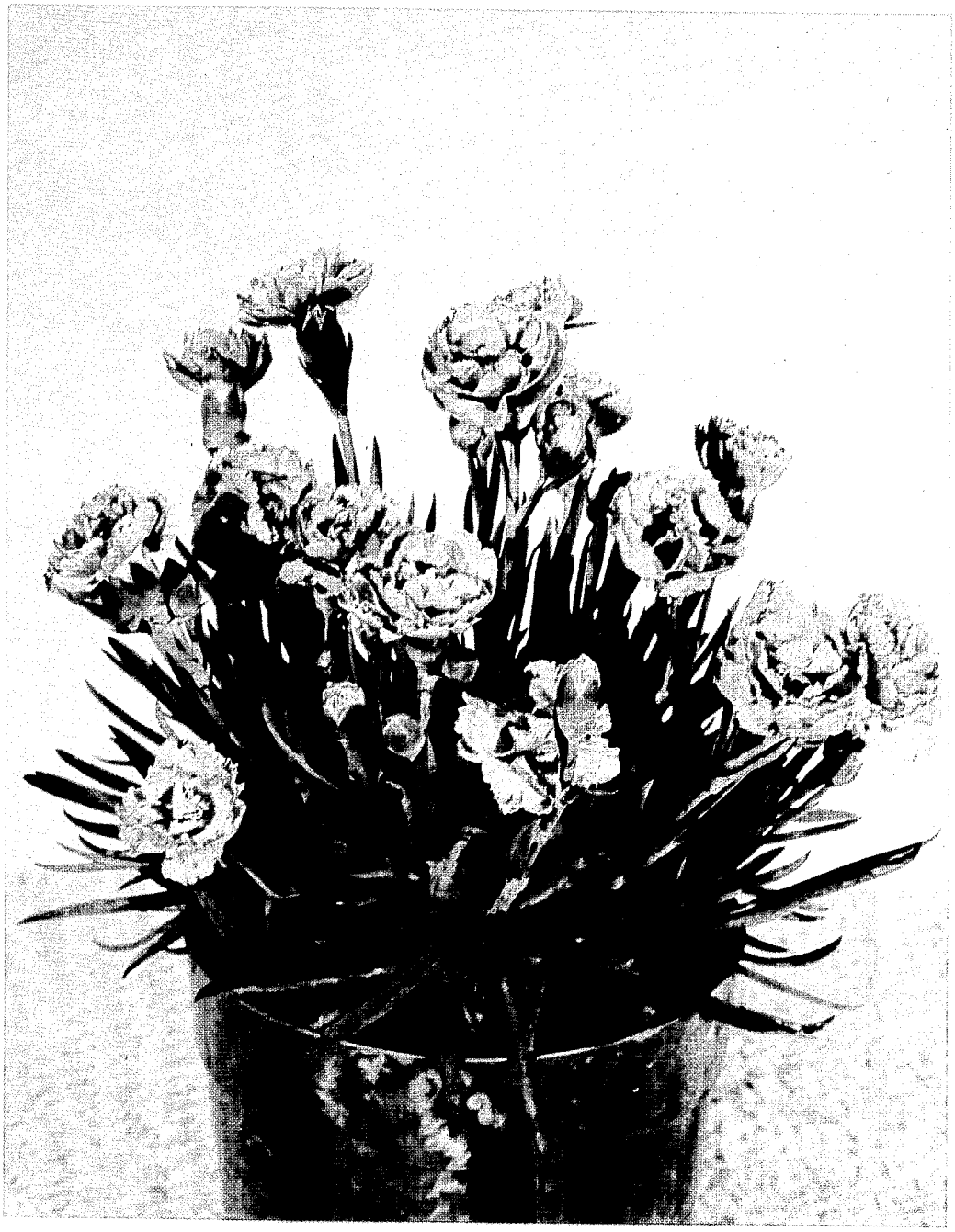
INVENTOR
JACOB R. MITTLEIDER
BY Herbert E. Kidder
AGENT United States Patent Office Plant Pat. 2,475
Patented Feb. 16, 1965

2,475
DIANTHUS PLANT

Jacob R. Mittleider, Loma Linda, Calif., assignor to Milo Academy, Inc., Milo, Oreg., a corporation of Oregon Filed Sept. 23, 1963, Ser. No. 310,959
1 Claim. (Cl. Plt.—70)

The present invention relates to a new and distinct variety of dianthus plant, which is characterized particularly by a low growing, compact, densely tufted plant bearing numerous medium-size double flowers of a distinctive shade of ashes of rose, with centers of dark rose, and having a faint, carnation-like fragrance.

The new and different plant variety is the result of an extensive breeding program at my nursery in Loma Linda, California, seeking new varieties of dianthus that would be especially suitable for mass plantings or edgings, without the necessity of staking the blooms. The characteristics sought were: (1) carnation foliage; (2) ever-blooming habit; (3) compactness; (4) fragrance; (5) large blooms; (6) strong stem; (7) hardiness and disease resistance, (8) pleasing new colors.

The present variety is a cross made by pollen from a Malmaison seedling on Dianthus Wallace Red, which is an unpatented hybrid of a *plumarius* species, parentage unknown. The Malmaison is a strain of carnation chiefly characterized by large size blooms, and used primarily for breeding purposes. The Wallace Red is used in this breeding step is a compact plant bearing non-fragrant, double flowers of red color. Seedlings from the first cross were then "selfed," which is a term for artificially pollinating the plants of a group having the same genes. Out of some ten thousand seedlings resulting from this last step, I found one outstanding plant having the desired characteristics of very low-growing, compact, bushy plant form, bearing many medium size, double flowers of ashes of rose color, with centers of darker rose, and having a faint carnation-like fragrance.

The original reproduction of the plant by cuttings was carried out in the experimental section of my nursery at Loma Linda, California. Asexual reproduction of my new variety by cuttings, as performed by me at the nursery, shows that the characteristics and distinctions of the variety come true to form and are established and transmitted through succeeding propagations.

The plant grows best in well-drained, loamy soil, but is not critical as to the pH of the soil. Best blooms are obtained when the plant is grown in full sunlight.

The accompanying drawing shows a typical plant of my new variety, showing the flowers and foliage depicted in color as nearly true as it is reasonably possible to make the same in a color illustration of this character.

The following is a detailed description of my new variety, as based on my observations of specimens grown at Loma Linda, California, with color terminology and identifications in accordance with "A Dictionary of Color" by Maerz and Paul.

Plant:

*Form.*—Compact, growing to a height of three to four inches.

*Growing habit.*—Densely tufted.

*Blooming habit.*—Floriferous, flowering evenly over the entire plant, with blossoms ranging from 1¼ to 1½ inches in diameter, and ranging in number from 3 or 4 on one year old plants grown in three inch pots, up to 20 or more on two year old plants.

*Blooming season.*—Perpetual in southern California, or wherever the mean temperature is above 50° F. Where the mean temperature drops below 50° F., the plant becomes dormant and ceases to bloom. Maximum bloom in southern California occurs from March through July, and in October and November; while minimum bloom occurs from August to October and from December through February.

*Foliage size.*—Maximum size of mature leaves on thrifty young plants is approximately 2 to 3 inches in length, by one-quarter inch in width.

*Quantity.*—Abundant.

*Shape.*—Lanceolate, or grass-like.

*Color.*—Growing under good conditions, the color of mature leaves is a deep true green, corresponding almost exactly to Aspen Green (Plate 31–C–6 in Maerz and Paul's Color Dictionary).

*Texture.*—Glaucous.

Flower:

*Size.*—The maximum size of the flowers is about 1¼ to 1½ inches in diameter by about ⅝ inch in width.

*Borne.*—At the end of the stem.

*Stem.*—Stiff and upright, approximately 4 to 6 inches in length.

*Petalage.*—Very double.

*Color.*—The flower is the color of ashes of rose (Plate 4–A–4, Maerz and Paul), with a center of darker rose (Plate 5–I–4, Maerz and Paul, Rose Petal).

*Petals.*—Firm in texture, of obovate form with regularly crenate margins. The size of the individual petal is about ¾ inch in length by ⅝ inch in width.

*Calyx.*—Spreading at the tip, with acuminate teeth, and approximately 1 inch in length.

Compared to other well-known dianthus plants, this new variety is distinguished by its low-growing, compact form and distinctive, faintly fragrant, ashes of rose flowers, with centers of a darker rose.

I claim:

A new and distinct variety of dianthus plant, substantially as shown and described herein, characterized particularly by its floriferous blooming habit, low-growing, compact, densely tufted plant form, usually not exceeding three to four inches in height, and bearing many very double flowers of ashes of rose color, with centers of darker rose, said flowers having a faint, carnation-like fragrance, and being borne on the ends of stiff, upright stems of approximately 4 to 6 inches in length.

No references cited.